United States Patent [19]

Sato et al.

[11] Patent Number: 5,438,139
[45] Date of Patent: Aug. 1, 1995

[54] ACRIDINIUM COMPOUNDS AND CONJUGATES THEREOF

[75] Inventors: Naofumi Sato, Saitama; Hiroshi Mochizuki, Tokyo; Toshinori Kanamori, Saitama, all of Japan

[73] Assignee: Mochida Pharmaceutical Co., Ltd., Tokyo, Japan

[21] Appl. No.: 188,724

[22] Filed: Jan. 31, 1994

[30] Foreign Application Priority Data

Feb. 4, 1993 [JP] Japan .................... 5-017465

[51] Int. Cl.$^6$ .................... C07D 219/08
[52] U.S. Cl. .................... 546/102; 546/104
[58] Field of Search .................... 546/104, 102

[56] References Cited

U.S. PATENT DOCUMENTS

| | | | |
|---|---|---|---|
| 4,745,181 | 5/1988 | Law et al. | 546/104 |
| 4,918,192 | 4/1990 | Law et al. | 546/104 |
| 4,950,613 | 8/1990 | Arnold, Jr. et al. | 546/104 |
| 5,110,932 | 5/1992 | Law et al. | 546/104 |
| 5,151,518 | 9/1992 | Dombrowski et al. | 546/104 |
| 5,227,489 | 7/1993 | Law et al. | 546/104 |
| 5,241,070 | 8/1993 | Law et al. | 546/104 |
| 5,281,712 | 1/1994 | McCapra et al. | 546/104 |
| 5,283,334 | 2/1994 | McCapra | 546/104 |
| 5,284,951 | 2/1994 | McCapra et al. | 546/104 |
| 5,284,952 | 2/1994 | Ramakrishnan | 546/104 |
| 5,321,136 | 6/1994 | McCapra | 546/104 |

FOREIGN PATENT DOCUMENTS

| | | |
|---|---|---|
| 263657 | 4/1988 | European Pat. Off. . |
| 324202 | 7/1989 | European Pat. Off. . |
| 63-101368 | 5/1988 | Japan . |
| 1199949 | 8/1989 | Japan . |
| 3501772 | 4/1991 | Japan . |
| 89/06231 | 7/1989 | WIPO . |

*Primary Examiner*—C. Warren Ivy
*Assistant Examiner*—A. A. Owens
*Attorney, Agent, or Firm*—Birch, Stewart, Kolasch & Birch

[57] ABSTRACT

Acridinium compounds represented by the general formula (I) where A is an intervening group which does not have activity for binding with a specific binding substance, Z is a labelling active group which has activity for binding with a specific binding substance, $R^1$ is a halogen atom, an alkyl group or an aryl group; $R^2$, $R^3$, $R^4$ and $R^5$ are each a hydrogen atom, an alkyl group, an aryl group, an alkoxy group, a nitro group, a halogen atom or a carbonyl group, and Y is a counter ion. The acridinium compounds may form conjugates with specific binding substances. The acridinium compounds have high emission efficiency and stability and, hence, are useful as chemiluminescence labelling agents.

12 Claims, 2 Drawing Sheets

ACRIDINIUM COMPOUNDS AND CONJUGATES THEREOF

BACKGROUND OF THE INVENTION

This invention relates to acridinium compounds and conjugates thereof. More particularly, the invention relates to acridinium compounds that are useful as chemiluminescent labelling agents because of their high emission efficiency and stability, as well as conjugates of such acridinium compounds and specific binding substances.

Acridinium esters have high emission efficiency and hence are useful as chemiluminescent labelling agents. In order for certain compounds to be practically useful as chemiluminescent labelling agents, it is generally essential that said compounds be highly stable in solution.

It is generally held that if the molecules of acridinium esters, taken as a whole, assume a planar structure on account of resonance, the strong electron withdrawing property of the acridinium ring causes electrons to be localized on the acridinium ring and, hence, the carbon atoms in the carbonyl group tend to become so much deficient of electrons that the esters are vulnerable to nucleophilic attack and, hence, labile. Under these circumstances, Unexamined Published Japanese Patent Application (kokai) Nos. Sho 63-101368 and Hei 3-501772 have disclosed acridinium esters that have an active group capable of binding with proteins and the like in the phenyl group or the 2-position of an acridinium group and which have a methyl group in the N-10 position, as well as a methyl group in the 2,6-position of the phenyl group.

Unexamined Published Japanese Patent Application (kokai) No. Hei 1-199949 teaches an acridinium ester having an active group capable of binding with proteins and the like in the N-10 position of the acridinium ring. The binding active group said acridinium ester has in the N-10 position is a bulky substituent such as a carboxymethyl group and, hence, steric hindrance is created between each of the hydrogen atoms in the 4,5-position of the acridinium ring and the substituents of nitrogen, rendering it difficult for the acridinium ring to assume a planar structure by itself; in this respect, the acridinium ester under consideration differs basically from the class of compounds that have a methyl group in the N-10 position and it would be advantageous from a stability viewpoint.

The acridinium esters which are taught in Unexamined Published Japanese Patent Application (kokai) Nos. Sho 63-101368 and Hei 3-501772 have another problem in that the functional group that has activity for binding with proteins and the like is bound to the benzene ring which is a leaving group, thereby putting considerable constraints when modifying the benzene ring. Further, the functional group having binding activity is highly reactive in itself and, hence, considerable difficulty is involved in the synthesis of these acridinium esters. In contrast, the acridinium ester which is taught in Unexamined Published Japanese Patent Application (kokai) No. Hei 1-199949 has activity for binding with proteins and the like in the N-10 position of the acridinium ring but it does not have any functional group for binding with proteins and the like in the leaving group. Therefore, it is fairly easy to modify the leaving group and, at the same time, the ester can be synthesized by a simple method since the only extra step that need be performed is to introduce the binding group at the final stage of synthesis. Because of these advantages, the acridinium ester under consideration has great utility in practical applications.

However, the acridinium ester compound that is specifically taught in Unexamined Published Japanese Patent Application (kokai) No. Hei 1-199949 is phenyl 10-carboxymethylacridinium-9-carboxylate bromide; since the benzene ring as a leaving group has no substituent, this compound has only low stability in solution and difficulty has been encountered with using it in practice as a labelling agents of specific binding substances.

SUMMARY OF THE INVENTION

The present invention has been accomplished under these circumstances and has as an object providing acridinium compounds that are useful as chemiluminescent labelling agents because of their high emission efficiency and stability.

Another object of the present invention is to provide conjugates of said acridinium compounds with specific binding substances.

The present inventors conducted extensive studies with a view to solving the aforementioned problems of the prior art and, as a result, they found that acridinium compounds that had binding groups introduced in the N-10 position of the acridinium ring and which had the benzene ring as a leaving group substituted by an alkyl group, an aryl group or a halogen in at least one ortho position had high emission efficiency and stability. The present invention has been accomplished on the basis of this finding.

Thus, according to its first aspect, the present invention provides acridinium compounds represented by the general formula ( I ):

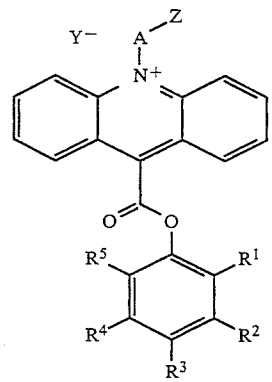

(where A is an alkylene group having 1–4 carbon atoms or an arylene group, in which one or more carbon atoms may be replaced by hetero atoms or which may optionally have substituents; Z is a carboxyl group, an alkoxycarbonyl group, a carbamoyl group, an aryloxycarbonyl group, a hydroxyl group, a cyano group, a carboxyimide group, an isocyanate group, an isothiocyanate group, an azide group, a sulfonic acid group, a sulfonamide group, a halogenated sulfonyl group, a halogenated carbonyl group, an N-succinimidyloxycarbonyl group or an N-phthalimidyloxycarbonyl group; $R^1$ is a halogen atom, an alkyl group or an aryl group; $R^2$, $R^3$, $R^4$ and $R^5$ which may be the same or different represent a hydrogen atom, an alkyl group, an aryl group, an alkoxy group, an acetyl group, a nitro group, a halogen atom or a carbonyl group, provided that adjacent groups as selected from among $R^2$, $R^3$, $R^4$ and $R^5$ may combine to form a ring; and Y is a counter ion).

According to its second aspect, the present invention provides conjugates of said acridinium compounds with specific binding substances.

DETAILED DESCRIPTION OF THE INVENTION

Figure 1:
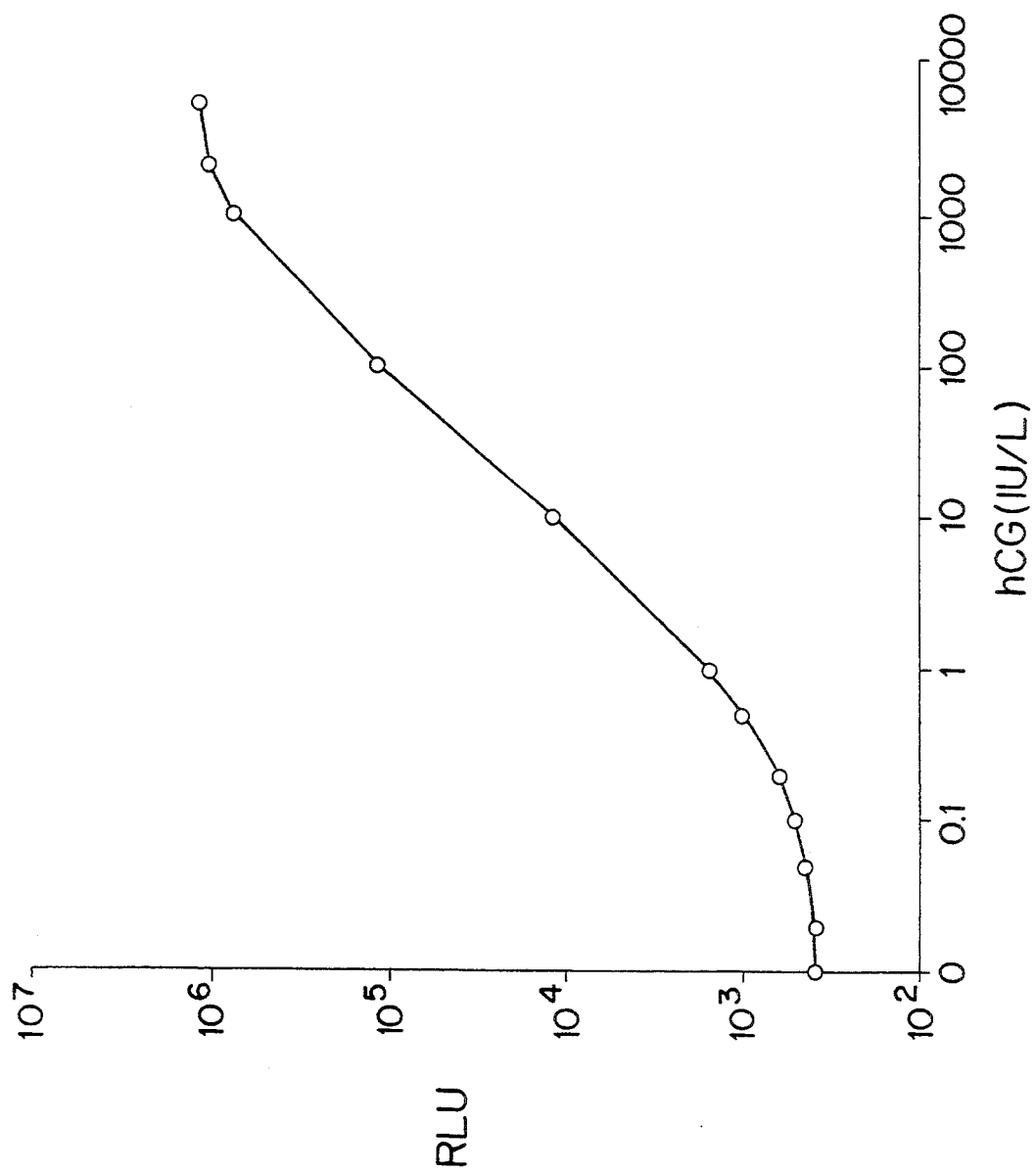
FIG. 1 is a graph showing the result of chemiluminescent immunoassay using the acridinium ester labelled antibody that was prepared in Example 28.

The acridinium compounds of the present invention (which are hereunder referred to as "the compounds of the present invention"), as well as conjugates of said acridinium compounds with specific binding substances are described below in detail.

In the general formula (I) which represents the compounds of the present invention, A is an intervening group which does not have activity for binding with any specific binding substances. Specifically, A is an alkylene group having 1-4 carbon atoms or an arylene group. Typical examples of the alkylene group having 1-4 carbon atoms are methylene, butylene, etc., and typical examples of the arylene group are phenylene, naphthylene, etc. One or more carbon atoms that compose A may be replaced by hetero atoms. Typical examples of such hetero atoms are oxygen, sulfur, etc. If desired, A may have one or more substituents and typical examples of such substituents include alkyl, aryl, alkylene, alkoxy, aryloxy, halogen, protected amino, protected hydroxyl, oxo, thio, imino, mercapto, etc.

In the general formula (I), Z is a binding group having activity for binding with specific binding substances and, specifically, Z is typified by a carboxyl group, an alkoxycarbonyl group, a carbamoyl group, an aryloxycarbonyl group, a hydroxyl group, a cyano group, a carboxyimide group, an isocyanate group, an isothiocyanate group, an azide group, a sulfonic acid group, a sulfonic acid amide group, a halogenated sulfonyl group, a halogenated carbonyl group, an N-succinimidyloxycarbonyl group or an N-phthalimidyloxycarbonyl group, etc.

In the general formula (I), $R^1$ is a halogen atom, an alkyl group or an aryl group and typical examples of $R^1$ include a chlorine atom, a methyl group and a phenyl group.

In the general formula (I), $R^2$, $R^3$, $R^4$ and $R^5$ may be the same or different and each represents a hydrogen atom, an alkyl group, an aryl group, an alkoxy group, an acetyl group, a nitro group, a halogen atom or a carbonyl group. Typical examples of the alkyl group are methyl, ethyl, etc. Typical examples of the aryl group are phenyl, naphthyl, etc. Typical examples of the alkoxy group are methoxy, ethoxy, etc. Typical examples of the halogen atom are chlorine, bromine, fluorine, etc. Adjacent groups as selected from among $R^2$, $R^3$, $R^4$ and $R^5$ may combine to form a ring such as a benzene or cyclohexane ring. If desired, $R^2$-$R^5$ may be such that adjacent R's combine to form a fused ring such as an aromatic or heterocyclic ring.

In the compounds of the present invention, $R^1$-$R^5$ also have no activity for binding with specific binding substances. For reasons associated with the structure of the leaving group, $R^1$, $R^2$, ... $R^5$ may be rearranged in the order $R^5$, $R^4$, ... $R^1$ and the resulting compound is same compound before rearrangement and is included within the scope of the present invention.

In the general formula (I), Y is a counter ion and specific examples include $CH_3SO_4^-$, $FSO_3^-$, $CF_3SO_3^-$, $C_4F_9SO_3^-$, a halogen ion, and the group represented by the following formula:

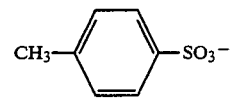

Among the compounds of the present invention which are represented by the above-defined general formula (I), those in which $R^1$ is an alkyl group, an aryl group or a halogen and wherein $R^2$-$R^5$ are each hydrogen are useful because they emit a large luminescence per molecule and are stable in solution and further because the starting materials are inexpensive and readily available. Particularly useful are an acridinium compound in which $R^1$ is a methyl group and $R^2$-$R^5$ are each hydrogen, as well as an acridinium compound in which $R^1$ is a phenyl group and $R^2$-$R^5$ are each hydrogen.

Acridinium compounds of the formula (I) in which $R^1$ is an alkyl group, an aryl group or a halogen, $R^5$ is an alkyl group or a halogen and $R^2$-$R^4$ are each hydrogen are also useful since they emit a large luminescence per molecule and are stable in solution and further because the starting materials are readily available, thus permitting easy synthesis of the desired compounds. Particularly useful are an acridinium compound in which $R^1$ is a methyl group, $R^5$ is chlorine and $R^2$-$R^4$ are each hydrogen, as well as an acridinium compound in which $R^1$ and $R^5$ are each chlorine and $R^2$-$R^4$ are each hydrogen.

Acridinium compounds of the formula (I) in which $R^1$ is an alkyl group, an aryl group or a halogen, either $R^2$ or $R^3$ is a nitro group, an acetyl group or a halogen, and in which $R^5$ is an alkyl group or $R^5$ forms a benzene ring with a $R^4$ adjacent thereto, with the other R's being hydrogen are also useful since they emit a large luminescence per molecule and are stable in solution. Particularly useful are the following: an acridinium compound in which $R^1$ and $R^5$ are both a methyl group, $R^3$ is a nitro group, and $R^2$ and $R^4$ are both hydrogen; an acridinium compound in which $R^1$ and $R^5$ are both a methyl group, $R^3$ is an acetyl group, and $R^2$ and $R^4$ are both hydrogen; an acridinium compound in which $R^1$ and $R^5$ are both a methyl group, $R^2$ is an acetyl group, and $R^3$ and $R^4$ are both hydrogen; and an acridinium compound in which $R^1$ is a methyl group, $R^3$ is an acetyl group and in which adjacent $R^4$ and $R^5$ fuse to form a benzene ring.

Specific examples of the compounds of the present invention are listed below under (I-a) to (I-h):

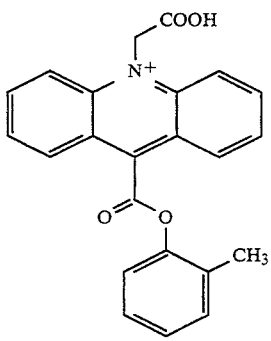
(I-a)

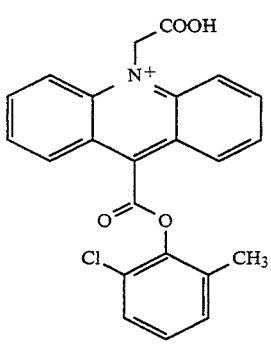
(I-b)

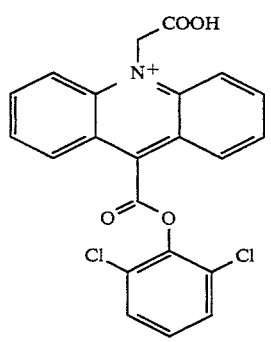
(I-c)

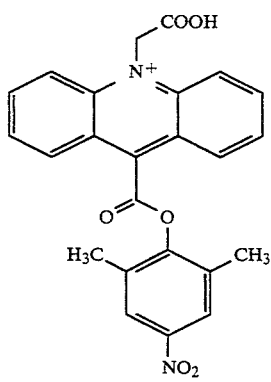
(I-d)

-continued

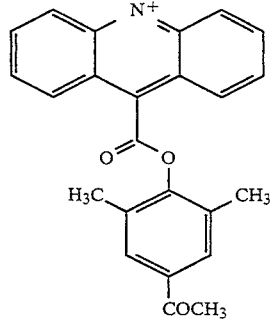
(I-e)

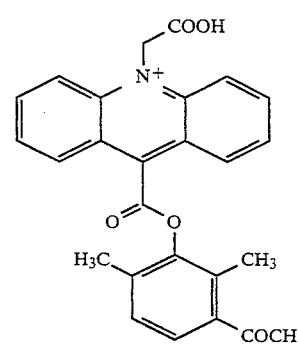
(I-f)

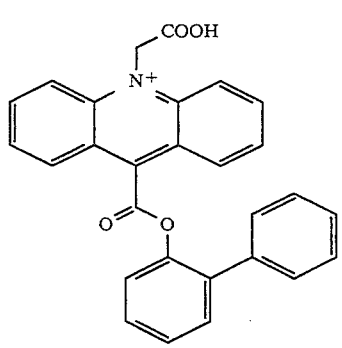
(I-g)

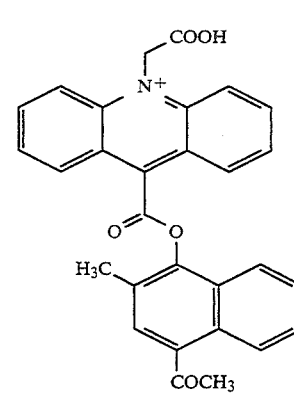
(I-h)

Among the compounds listed above, 2'-methylphenyl acridinium-9-carboxylate trifluoromethanesulfonate which is represented by the formula (I-a) is particularly useful since the starting materials are cheap, readily available and the reaction steps are simple enough to permit easy synthesis and further because the synthesized product has high stability.

The production of the compounds of the present invention may typically proceed as follows. First, a phenol derivative that corresponds to the desired acridinium compound is reacted with an acridine carboxylic acid derivative in the presence of a condensing agent to form a phenol ester of acridine carboxylic acid. Then, the resulting phenol ester of acridine carboxylic acid is alkylated in the N-10 position with an alkylating agent, thereby giving an acridinium ester. Stated more specifically, a phenol derivative is reacted with 9-chlorocarbonylacridine in a solvent in the presence of a base to give an acridine carboxylic acid phenol ester. Examples of the base that can be used in this reaction include triethylamine and pyridine, and examples of the solvent include dichloromethane, ether and toluene, with dichloromethane being preferred.

In the next step, an alkylating agent having a binding functional group protected with a protective group is reacted with the prepared acridine carboxylic acid phenol ester in a solvent or in the absence of a solvent, thereby giving an acridinium ester having the protected binding group. Examples of the alkylating agent that may be used in this reaction and which has a binding group protected with a suitable protective group include an alkyl halide substituted by a carboxylic acid that is protected with a substituted benzyl group or a t-butyl group, and an alkyl ester of a superstrong acid such as trifluoromethanesulfonic acid, preferably an alkyl ester of trifluoromethanesulfonic acid. If a solvent is to be used, exemplary solvents include dichloromethane and chloroform.

Further, an acid catalyst is allowed to act on the resulting acridinium ester having the protected binding group in the presence or absence of a solvent, whereby the acridinium compound of the present invention is produced. If a solvent is to be used in this reaction, exemplary solvents that can be used include acetic acid, dichloromethane, etc., and examples of the acid catalyst that can be used include hydrobromic acid, trifluoromethylacetic acid, etc.

The compounds of the present invention feature high emission efficiency and stability and because of these properties, the compounds are useful as labelling agents of specific binding substances including antigens, antibodies and nucleic acids.

According to its second aspect, the present invention provides conjugates in which the acridinium compounds represented by the general formula (I) defined above bind with specific binding substances solely via the active group Z. The conjugates are such that the acridinium compounds represented by the general formula (I) bind either directly or indirectly to specific binding substances via Z.

The specific binding substances which are bound to the acridinium compounds of the present invention refer to a class of those substances which, in the combination of a substance having a certain specified structure with a substance that binds specifically to said first substance, fall in the category of either one of two such substances. Exemplary members in combination include the following: an antigen and an antibody; a nucleic acid and a complementary nucleic acid sequence; an effector molecule and a receptor molecule, an enzyme and an inhibitor; avidin and biotin; a substance having a sugar chain and a lectin; etc.

In the conjugates of the present invention, the acridinium compounds represented by the general formula (I) are bound to the specific binding substances through covalent bonds.

To prepare the conjugates of the present invention, the acridinium compounds represented by the general formula (I) may be bound to specific binding substances by generally chemical reactions. Take, for example, the case where the specific binding substance is a protein and the binding site in the structure of the specific binding substance is an amino group; then, Z is preferably selected from among $-SO_2Cl$, N-succinimidyl group, N-phthalimide group, $-COOH$, $-COCl$, $-N=C=S$, etc. To have Z bound to the specific binding substance, one may use any of the known methods that are described in "Koso Meneki Sokuteiho (Enzyme Immunoassay Techniques)", 3rd Ed., Compiled by Yeiji Ishikawa et al., Igaku Shoin, 75–151, 1987. Exemplary methods that can be used include those which rely upon dehydrative condensation reaction, as illustrated by the mixed acid anhydride procedure and the active esterification procedure using succinimide and the like, as well as the one that relies upon addition reaction using a thioisocyanate or azide.

If the acridinium compounds represented by the general formula(I) are to be bound indirectly to the specific binding substances, the two materials may be intervened with a protein such as bovine serum albumin (BSA) or any known substance that is as a crosslinking agent.

The conjugates of the present invention are of such a form that N in the 10-position of the acridinium ring binds to a very large molecule and the resulting increase in the distortion of the acridinium ring renders the conjugates stable. Hence, the conjugates will prove very useful in various applications of chemiluminescent substances, such as immunochemical assays, DNA probe assays, and receptor assays.

The following examples are provided for the purpose of further illustrating the present invention but are in no way to be taken as limiting.

EXAMPLE 1

(1) Synthesis of 2'-methylphenyl acridine-9-carboxylate

Acridine-9-carboxylic acid (0.42 g, 1.87 mmol) was suspended in thionyl chloride (10 ml) and the suspension was refluxed under heating for 2 h. Excess thionyl chloride was distilled off the reaction mixture under reduced pressure to give 9-chlorocarbonylacridine hydrochloride (0.5 g, 96%). Then, the resulting 9-chlorocarbonylacridine hydrochloride (0.5 g) and 2-methylphenol (0.2 g, 1.9 mmol) were suspended in dichloromethane (15 ml) and triethylamine (1.0 ml) and a catalytic amount of dimethylaminopyridine were added to the suspension with stirring. The reaction mixture was stirred at room temperature for 15 h and thereafter washed with 1 N HCl, water, a 5% aqueous solution of sodium hydrogencarbonate and a saturated aqueous solution of sodium chloride in the order written. The organic layer was separated and dried over anhydrous sodium sulfate, followed by evaporation of the solvent under reduced pressure. The residue was purified by silica gel column chromatography using a dichloromethane-hexane mixture as eluant, giving the desired compound, 2'-methylphenyl acridine-9-carboxylate, in an amount of 0.33 g.

$^1$H-NMR: δ2.37 (3H, s), 7.3–8.3 (12H, m) MS: M+313

(2) Synthesis of 2'-methylphenyl 10-carboxymethylacridinium-9-carboxylate trifluoromethanesulfonate The 2'-methylphenyl acridine-9-carboxylate (142 mg, 0.45 mmol) which was prepared in (1) above was dissolved in dichloromethane (1 ml). To the solution, benzyloxycarbonylmethyl trifluoromethanesulfonate (1.4 g) was added as it was prepared by the method described in Angew. Chem., 98, p. 264 (1986). Thereafter, reaction was carried out with stirring the mixture at room temperature for 4 days in an argon atmosphere. Ether (20 ml) was added to the reaction mixture and the resulting precipitate was separated by filtration and then washed with ether. The resulting 2'-methylphenyl 10-benzyloxycarbonylmethyl-acridinium-9-carboxylate trifluoromethanesulfonate was added to a solution (5 ml) of 25% hydrobromic acid in acetic acid and the reaction was carried out with stirring at 50° C. for 2 h. Ether (100 ml) was added to the reaction mixture and the resulting precipitate was separated by filtration. The resulting crude product was washed with ether and purified by reverse-phase HPLC, giving the desired compound, 2'-methylphenyl 10-carboxymethylacridinium-9-carboxylate trifluoromethanesulfonate (hereunder abbreviated as "MAC-2") in an amount of 202 mg.

MS: M+372

EXAMPLE 2

(1) Synthesis of 2'-biphenyl acridine-9-carboxylate

The procedure of Synthesis (1) in Example 1 was repeated, except that the starting materials were 9-chlorocarbonylacridine hydrochloride (0.5 g, 1.8 mmol) and 2-phenylphenol (0.33 g, 1.9 mmol). As a result, 2'-biphenyl acridine-9-carboxylate was given in an amount of 0.57 g.

$^1$H-NMR: δ7.3–8.3 ( 17H, m) MS: M+375

(2) Synthesis of 2'-biphenyl 10-carboxymethylacridinium-9-carboxylate trifluoromethanesulfonate Using the 2'-biphenyl acridine-9-carboxylate (36 mg, 0.1 mmol) which was prepared in (1) above, the procedure of Synthesis (2) in Example 1 was repeated, giving the desired compound, 2'-biphenyl 10-carboxymethylacridinium-9-carboxylate trifluoromethanesulfonate (hereunder abbreviated as "MAC-3") in an amount of 50 mg.

MS: M+434

EXAMPLE 3

(1) Synthesis of 2'-methyl-6'-chlorophenyl acridine-9-carboxylate.

The procedure of Synthesis (1) in Example 1 was repeated, except that the starting materials were 9-chlorocarbonylacridine hydrochloride (0.5 g, 1.8 mmol) and 2-methyl-6-chlorophenol (0.28 g, 1.9 mmol). As a result, 2'-methyl-6'-chlorophenyl acridine-9-carboxylate was given in an amount of 0.46 g.

$^1$H-NMR: δ2.43(3H, s), 7.2–8.6(11H, m) MS: M+347

(2) Synthesis of 2'-methyl-6'-chlorophenyl 10-carboxymethylacridinium- 9-carboxylate trifluoromethanesulfonate.

Using the 2'-methyl-6'-chlorophenyl acridine-9-carboxylate (28 mg, 0.08 retool) which was prepared in (1) above, the procedure of Synthesis (2) in Example 1 was repeated, giving the desired compound, 2'-methyl-6'-chlorophenyl 10-carboxymethylacridinium-9-carboxylate trifluoromethanesulfonate (hereunder abbreviated as "MAC-4") in an amount of 30 mg.

MS: M+406

EXAMPLE 4

(1) Synthesis of 2', 6'-dichlorophenyl acridine-9-carboxylate.

The procedure of Synthesis (1) in Example 1 was repeated, except that the starting materials were 9-chlorocarbonylacridine hydrochloride (0.5 g, 1.8 mmol) and 2,6-dichlorophenol (0.32 g, 1.9 mmol) As a result, 2'6-dichlorophenyl acridine-9-carboxylate was given in an amount of 0.42 g.

$^1$H-NMR: δ7.3–8.7 (11H, m) MS: M+357

(2) Synthesis of 2',6'-dichlorophenyl 10-carboxymethylacridinium- 9-carboxylate trifluoromethanesulfonate.

Using the 2', 6'-dichlorophenyl acridine-9-carboxylate (25 mg, 0.07 mmol) which was prepared in (1) above, the procedure of Synthesis (2) in Example 1 was repeated, giving the desired compound, 2', 6'-dichlorophenyl 10-carboxymethylacridinium- 9-carboxylate trifluoromethanesulfonate (hereunder abbreviated as "MAC-5") in an amount of 28 mg.

MS: M+416

EXAMPLE 5

(1) Synthesis of 2', 6'-dimethyl-4'-nitrophenyl acridine-9-carboxylate.

The procedure of Synthesis (1) in Example 1 was repeated, except that the starting materials were 9-chlorocarbonylacridine hydrochloride (0.5 g, 1.8 mmol) and 2,6-dimethyl-4-nitrophenol (0.33 g, 1.9 retool) . As a result, 2', 6'-dimethyl-4'-nitrophenyl acridine-9-carboxylate was given in an amount of 0.50 g.

$^1$H-NMR: δ2.52 (6H, s), 7.9–8.4 (10H, m) MS: M+372.

(2) Synthesis of 2', 6'-dimethyl-4'-nitrophenyl 10-carboxymethylacridinium-9-carboxylate trifluoromethanesulfonate.

Using the 2', 6'-dimethyl-4'-nitrophenyl acridine-9-carboxylate (12 mg, 0.03 mmol) which was prepared in (1) above, the procedure of Synthesis (2) in Example 1 was repeated, giving the desired compound, 2', 6'-dimethyl-4'-nitrophenyl 10-carboxymethylacridinium-9-carboxylate trifluoromethanesulfonate (hereunder abbreviated as "MAC-6") in an amount of 8 mg.

MS: M+431

EXAMPLE 6

(1) Synthesis of 2,6-dimethyl-4-acetylphenol.

To an ice-cooled solution of 2,6-dimethylphenol (12.2 g, 0.1 mmol) in dichloromethane, anhydrous aluminum chloride (14.4 g) was slowly added with stirring, followed by slow addition of acetyl chloride (9.4 g) . The reaction mixture was stirred at 10° C. or below for 1 h, then at room temperature for 3 h. Thereafter, the mixture was poured into ice water. Then, the reaction product was extracted with dichloromethane and the extracted layer was washed with water. Further, the extracted layer was dried over anhydrous sodium sulfate and the solvent was distilled off under reduced pressure. The residue was recrystallized with benzene, giving the desired compound, 2,6-dimethyl-4-acetylphenol in an amount of 1.9 g.

$^1$H-NMR: δ2.25(6H, s), 2.51 (3H, s), 5.7 (1H, br), 7.51 (2H, s)

MS: M+164

(2) Synthesis of 2', 6'-dimethyl-4'-acetylphenyl acridine-9-carboxylate.

The procedure of Synthesis (1) in Example 1 was repeated, except that the 2, 6-dimethyl-4-acetylphenol (0.30 g) which was prepared in (1) above and 9-chlorocarbonylacridine hydrochloride (0.5 g, 1.8 mmol) were used as starting materials As a result, 2', 6'-dimethyl-4'-acetylphenyl acridine-9-carboxylate was given in an amount of 0.54 g.

1H-NMR: δ2.50(6H, s), 2.64(3H, s), 7.6–8.5(10H, m) MS: M+369

(3) Synthesis of 2′, 6′-dimethyl-4′-acetylphenyl 10-carboxymethylacridinium-9-carboxylate trifluoromethanesulfonate.

Using the 2′, 6′-dimethyl-4′-acetylphenyl acridine-9-carboxylate (26 mg, 0.07 mmol) which was prepared in (2) above, the procedure of Synthesis (2) in Example 1 was repeated, giving the desired compound, 2′, 6′-dimethyl-4′-acetylphenyl 10-carboxymethylacridinium-9-carboxylate trifluoromethanesulfonate (hereunder abbreviated as "MAC-7") in an amount of 16 mg.
MS: M+428

EXAMPLE 7

(1) Synthesis of 2,4-dimethyl-3-nitroacetophenone.

To a cooled liquid mixture of fuming nitric acid and acetic anhydride, 2,4-dimethylacetophenone (75 g, 0.5 mol) was slowly added and the mixture was stirred at 10° C. or below for 3 h. The reaction mixture was poured into ice water and the resulting precipitate was separated by filtration. The separated precipitate was dissolved in ethyl acetate and the solution was washed with saturated sodium hydrogencarbonate and water in the order written. Thereafter, the solution was dried over anhydrous sodium sulfate and concentrated under reduced pressure. The residue was purified by silica gel column chromatography using a hexane-ethyl acetate mixture as eluant, giving the desired compound, 2,4-dimethyl-3-nitroacetophenone, in an amount of 8.9 g.

$^1$H-NMR: δ2.32(3H, s), 2.38(3H, s), 2.56(3H, s), 3.3(1H, br), 7.38(2H, dd, J=8 Hz, 25 Hz) MS: M+193.
(2) -Synthesis of 2,4-dimethyl-3-aminoacetophenone.

The 2,4-dimethyl-3-nitroacetophenone (8.9 g, 46 mmol) which was prepared in (1) above was dissolved in ethanol and 10% palladium-carbon (100 mg) was added to the solution, and hydrogen gas was blown into the solution with stirring for 1.5 h. The palladium-carbon catalyst was filtered off the reaction mixture and the filtrate was concentrated under reduced pressure to give the desired compound, 2,4-dimethyl-3-aminoacetophenone, in an amount of 7.5 g.
MS: M+163
(3) Synthesis of 2,4-dimethyl-3-hydroxyacetophenone.

The 2,4-dimethyl-3-aminoacetophenone (7.5 g, 46 mmol) which was prepared in (2) above was dissolved in 1.5 N HCl. The solution was ice cooled while sodium nitrite (3.3 g) as dissolved in water (17 ml) was added with stirring. The mixture was subjected to reaction under ice cooling for 1 h, then by refluxing under heating for 15 h. The reaction mixture was subjected to extraction with dichloromethane and the extracted layer was washed with water. Thereafter, the washed layer was dried over anhydrous sodium sulfate and the solvent was distilled off under reduced pressure. The residue was purified by silica gel column chromatography with a hexane-ethyl acetate mixture used as eluant, giving the desired compound, 2,4-dimethyl-3-hydroxyacetophenone, in an amount of 1.2 g.

$^1$H-NMR: δ2.25(3H, s), 2.36(3H, s), 2.54(3H, s), 5.31(1H, br), 7.03(2H, dd, J=8 Hz, 18 Hz) MS: M+164.
(4) Synthesis of 2′, 6′-dimethyl-3′-acetylphenyl acridine-9-carboxylate.

The procedure of Synthesis (1) in Example 1 was repeated, except that the 2,4-dimethyl-3-hydroxyacetophenone (0.30 g, 1.8 mmol) which was prepared in (3) above and 9-chlorocarbonylacridine hydrochloride (0.5 g, 1.8 mmol) were used as starting materials. As a result, the desired compound, 2′, 6′-dimethyl-3′-acetylphenyl acridine-9-carboxylate, was given in an amount of 0.36 g.

$^1$H-NMR: δ2.53(6H, s), 2.64(3H, s), 7.3–7.9(8H, m), 8.37(2H, dd, J=8 Hz, 10 Hz) MS: M+369
(5) Synthesis of 2′, 6′-dimethyl-3′-acetylphenyl 10-carboxymethylacridinium-9-carboxylate trifluoromethanesulfonate.

Using the 2′, 6′-dimethyl-3′-acetylphenyl acridine-9-carboxylate (20 mg, 0.06 mmol) which was prepared in (4) above, the procedure of Synthesis (2) in Example 1 was repeated, giving the desired compound, 2′, 6′-dimethyl-3′-acetylphenyl 10-carboxymethylacridinium-9-carboxylate trifluoromethanesulfonate (hereunder abbreviated as "MAC-8"), in an amount of 21 mg.
MS: M+428

EXAMPLE 8

(1) Synthesis of 2′, 6′-dimethyl-4′-chlorophenyl acridine-9-carboxylate.

The procedure of Synthesis (1) in Example 1 was repeated, except that the starting materials were 9-chlorocarbonylacridine hydrochloride (0.5 g, 1.8 mmol) and 2,6-dimethyl-4-chlorophenol (0.30 g, 1.9 mmol). As result, 2′, 6′-dimethyl-4′-chlorophenyl acridine-9-carboxylate was given in an amount of 0.44 g.

$^1$H-NMR: δ2.41(6H, s), 7.2–8.5(10H, m) MS: M+361.
(2) Synthesis of 2′, 6′-dimethyl-4′-chlorophenyl 10-carboxymethylacridinium-9-carboxylate trifluoromethanesulfonate.

Using the 2′, 6′-dimethyl-4′-chlorophenyl acridine-9-carboxylate (36 mg, 0.10 mmol) which was prepared in (1) above, the procedure of Synthesis (2) in Example 1 was repeated, giving the desired compound, 2′, 6′-dimethyl-4′-chlorophenyl 10-carboxymethylacridinium-9-carboxylate trifluoromethanesulfonate (hereunder abbreviated as "MAC-9"), in an amount of 47 mg.
MS: M+420

EXAMPLE 9

(1) Synthesis of 2′, 6′-dimethyl-4′-bromophenyl acridine-9-carboxylate.

The procedure of Synthesis (1) in Example 1 was repeated, except that the starting materials were 9-chlorocarbonylacridine hydrochloride (0.5 g, 1.8 mmol) and 2,6-dimethyl-4-bromophenol (0.39 g, 1.9 mmol). As a result, 2′, 6′-dimethyl-4′-bromophenyl acridine-9-carboxylate was given in an amount of 0.41 g.

$^1$H-NMR: δ2.41(6H, s), 7.3–8.4(10H, m) MS: M+406.
(2) Synthesis of 2′, 6′-dimethyl-4′-bromophenyl 10-carboxymethylacridinium-9-carboxylate trifluoromethanesulfonate.

Using the 2′, 6′-dimethyl-4′-bromophenyl acridine-9-carboxylate (38 mg, 0.09 mmol) which was prepared in (1) above, the procedure of Synthesis (2) in Example 1 was repeated, giving the desired compound, 2′, 6′-dimethyl-4′-bromophenyl 10-carboxymethylacridinium-9-carboxylate trifluoromethanesulfonate (hereunder abbreviated as "MAC-10") in an amount of 46 mg.
MS: M+465

EXAMPLE 10

(1) Synthesis of 2-methyl-4-acetyl-l-naphthol.

To an ice-cooled solution of 2-methyl-l-naphthol (7.9 g, 0.05 mmol) in dichloromethane, anhydrous aluminum chloride (7.2 g) was slowly added with stirring, followed by slow addition of acetyl chloride (4.7 g) to start reaction. The reaction mixture was stirred at 10° C. or below for 1 h, then at room temperature for 3 h. Thereafter, the mixture was poured into ice water. Then, the reaction product was extracted with dichloromethane and the extracted layer was washed with water. Further, the extracted layer was dried over anhydrous sodium sulfate and the solvent was distilled off under reduced pressure. The residue was recrystallized with benzene, giving the desired compound, 2-methyl-4-acetyl-1-naphthol, in an amount of 3.9 g.

$^1$H-NMR: δ2.45(3H, s), 2.71(3H, s), 5.8(1H, br), 7.3–9.0(5H, m) MS: M+200.

(2) Synthesis of 1'-(2'-methyl-4'-acetyl) naphthylacridine-9-carboxylate.

The procedure of Synthesis (1) in Example 1 was repeated, except that the 2-methyl-4-acetyl-1-naphthol (0.36 g, 1.8 mmol) which was prepared in (1) above and 9-chlorocarbonylacridine hydrochloride (0.5 g, 1.8 mmol) were used as starting materials. As a result, the desired compound, 1'-(2'-methyl-4'-acetyl) naphthylacridine-9-carboxylate, was given in an amount of 0.67 g.

$^1$H-NMR: δ2.76(3H, s), 2.80(3H, s), 7.5–8.8(13H, m) MS: M+405.

(3) Synthesis of 1'-(2'-methyl-4'-acetyl) naphthyl-10-carboxymethylacridinium-9-carboxylate trifluoromethanesulfonate.

Using the 1'-(2'-methyl-4'-acetyl) naphthylacridine-9-carboxylate (33 mg, 0.08 mmol) which was prepared in (2) above, the procedure of Synthesis (2) in Example 1 was repeated, giving the desired compound, 1'-(2'-methyl-4'-acetyl) naphthyl-10-carboxymethylacridinium-9-carboxylate trifluoromethanesulfonate (hereunder abbreviated as "MAC-11"), in an amount of 35 mg.

MS: M+464

EXAMPLE 11

(1) Synthesis of 2'-methylphenyl acridine-9-carboxylate.

A benzyl ester of 6-iodopentanoic acid (2.4 g) was prepared by the method described in J. Pharm. Sci., 77, p. 855 (1988) and added to the 2'-methylphenyl acridine-9-carboxylate (30 mg, 0.10 mmol) which was prepared in Example 1. Thereafter, the mixture was subjected to reaction at 110° C. for 24 h with stirring. Ether was added to the reaction mixture; the resulting precipitate was separated by filtration and washed with ether. The resulting 2'-methylphenyl 10-benzyloxycarbonylbutylacridinium-9-carboxylate iodide was added to a 25% solution (5 ml) of hydrobromic acid in acetic acid and reaction was carried out at 50° C. for 2 h with stirring. Thereafter, ether was added to the reaction mixture and the resulting precipitate was separated by filtration. The separated precipitate was washed with ether and purified by reverse-phase HPLC, giving the desired compound, 2'-methylphenyl 10-carboxybutylacridinium-9-carboxylate bromide (hereunder abbreviated as "MAC-12") in an amount of 30 mg.

MS: M+414

EXAMPLE 12

(1) Synthesis of 2'-methyl-4'-fluorophenyl acridine-9-carboxylate.

The procedure of Synthesis (1) in Example 1 was repeated, except that the starting materials were 9-chlorocarbonylacridine hydrochloride (0.5 g, 1.8 mmol) and 2-methyl-4-fluorophenol (0.24 g, 1.9 mmol). As a result, the desired compound, 2'-methyl-4'-fluorophenyl acridine-9-carboxylate, was given in an amount of 0.46 g.

$^1$H-NMR: δ2.37(3H, s), 7.0–8.4(11H, m) MS: M+331

(2) Synthesis of 2'-methyl-4'-fluorophenyl 10-carboxymethylacridinium-9-carboxylate trifluoromethanesulfonate.

Using the 2'-methyl-4'-fluorophenyl acridine-9-carboxylate (31 mg, 0.09 mmol) which was prepared in (1) above, the procedure of Synthesis (2) in Example 1 was repeated, giving the desired compound, 2'-methyl-4'-fluorophenyl 10-carboxymethylacridinium-9-carboxylate trifluoromethanesulfonate (hereunder abbreviated as "MAC-13"), in an amount of 49 mg.

MS: M+390

EXAMPLE 13

(1) Synthesis of 2-methyl-6-nitrophenol.

To an ice-cooled solution of 2-methylphenol (10.8 g, 0.1 mmol) in acetic acid, fuming nitric acid (6.3 g) was slowly added with stirring to start reaction. The reaction mixture was stirred at a temperature of 20° C. or below for 1 h and thereafter poured into ice water. The reaction product was extracted with ethyl acetate and the extracted layer was washed with water, saturated sodium hydrogencarbonate and a saturated aqueous solution of sodium chloride in the order written. Thereafter, the washed layer was dried over anhydrous sodium sulfate and the solvent was distilled off under reduced pressure. The residue was purified by silica gel column chromatography with a benzene-ethyl acetate mixture used as eluant, thereby giving the desired compound, 2-methyl-6-nitrophenol, in an amount of 1.3 g.

$^1$H-NMR: δ2.29(3H, s), 5.7(1H, br), 6.7–8.0(3H, m) MS: M+153.

(2) Synthesis of 2'-methyl-6'-nitrophenyl acridine-9-carboxylate.

The procedure of Synthesis (1) in Example 1 was repeated, except that the 2-methyl-6-nitrophenol (0.28 g, 1.8 mmol) which was prepared in (1) above and 9-chlorocarbonylacridine hydrochloride (0.5 g, 1.8 mmol) were used as starting materials. As a result, 2'-methyl-6'-nitrophenyl acridine-9-carboxylate was given in an amount of 0.53 g.

$^1$H-NMR: δ2.46(3H, s), 7.4–8.6(11H, m) MS: M+358.

(3) Synthesis of 2'-methyl-6'-nitrophenyl 10-carboxymethylacridinium-9-carboxylate trifluoromethanesulfonate.

Using the 2'-methyl-6'-nitrophenyl acridine-9-carboxylate (24 mg, 0.07 mmol) which was prepared in (2) above, the procedure of Synthesis (2) in Example 1 was repeated, giving the desired compound, 2'-methyl-6'-nitrophenyl 10-carboxymethylacridinium-9-carboxylate trifluoromethanesulfonate (hereunder abbreviated as "MAC-14") in an amount of 12 mg.

MS: M+417

EXAMPLE 14

(1) Synthesis of 2', 6'-dibromophenyl acridine-9-carboxylate.

The procedure of Synthesis (1) in Example 1 was repeated, except that the starting materials were 9-chlorocarbonylacridine hydrochloride (0.5 g, 1.8 mmol) and 2,6-dibromophenol (0.49 g, 1.9 mmol). As a result, 2', 6'-dibromophenyl acridine-9-carboxylate was given in an amount of 0.55 g.

$^1$H-NMR: δ7.0–8.8(11H, m) MS: M+457.

(2) Synthesis of 2', 6'-dibromophenyl 10-carboxymethylacridinium-9-carboxylate trifluoromethanesulfonate.

Using the 2', 6'-dibromophenyl acridine-9-carboxylate (35 mg, 0.08 mmol) which was prepared in (1)

above, the procedure of Synthesis (2) in Example 1 was repeated, giving the desired compound, 2', 6'-dibromophenyl 10-carboxymethylacridinium-9-carboxylate trifluoromethanesulfonate (hereunder abbreviated as "MAC-15"), in an amount of 36 mg.
MS: M+516

EXAMPLE 15

(1) Synthesis of 2'-fluoro-6'-methoxyphenyl acridine-9-carboxylate.

The procedure of Synthesis (1) in Example 1 was repeated, except that the starting materials were 9-chlorocarbonylacridine hydrochloride (0.5 g, 1.8 mmol) and 2-fluoro-6-methoxyphenol (0.28 g, 1.9 mmol). As a result, 2'-fluoro-6'-methoxyphenyl acridine-9-carboxylate was given in an amount of 0.39 g.
$^1$H-NMR: δ4.03(3H, s), 6.8–8.5(11H, m) MS: M+347.

(2) Synthesis of 2'-fluoro-6'-methoxyphenyl 10- carboxymethylacridinium-9-carboxylate trifluoromethanesulfonate.

Using the 2'-fluoro-6'-methoxyphenyl acridine-9-carboxylate (19 mg, 0.05 mmol) which was prepared in (1) above, the procedure of Synthesis (2) in Example 1 was repeated, giving the desired compound, 2'-fluoro-6'-methoxyphenyl 10-carboxymethylacridinium-9-carboxylate trifluoromethanesulfonate (hereunder abbreviated as "MAC-16"), in an amount of 30 mg.
MS: M+406

EXAMPLE 16

(1) Synthesis of 2'-methyl-4', 6'-dichlorophenyl acridine -9-carboxylate.

The procedure of Synthesis (1) in Example 1 was repeated, except that the starting materials were 9-chlorocarbonylacridine hydrochloride ( 0.5 g, 1.8 mmol) and 2-methyl-4,6-dichlorophenol (0.34 g, 1.9 mmol). As a result, 2'-methyl-4', 6'-dichlorophenyl acridine-9-carboxylate was given in an amount of 0.36 g.
$^1$H-NMR: δ2.41(3H, s), 7.3–8.6(10H, m) MS: M+381.

(2) Synthesis of 2'-methyl-4', 6'-dichlorophenyl 10-carboxymethylacridinium-9-carboxylate trifluoromethane sulfonate.

Using the 2'-methyl-4', 6'-dichlorophenyl acridine-9-carboxylate (39 mg, 0.10 mmol) which was prepared in (1) above, the procedure of Synthesis (2) in Example 1 was repeated, giving the desired compound, 2'-methyl-4', 6'-dichlorophenyl 10-carboxymethylacridinium-9-carboxylate trifluoromethanesulfonate (hereunder abbreviated as "MAC-17") in an amount of 28 mg.
MS: M+440

EXAMPLE 17

( 1 ) Synthesis of 2', 4', 6'-trichlorophenyl acridine-9-carboxylate.

The procedure of Synthesis (1) in Example 1 was repeated, except that the starting materials were 9-chlorocarbonylacridine hydrochloride (0.5 g, 1.8 mmol) and 2,4,6-trichlorophenol (0.38 g, 1.9 mmol). As a result, 2', 4', 6'-trichlorophenyl acridine-9-carboxylate was given in an amount of 0.59 g.
$^1$H-NMR: δ7.5–8.6 (10H, m) MS: M+401.

(2) Synthesis of 2', 4', 6'-trichlorophenyl 10- carboxymethylacridinium-9-carboxylate trifluoromethanesulfonate.

Using the 2', 4', 6'-trichlorophenyl acridine-9-carboxylate (27 mg, 0.06 mmol) which was prepared in (1) above, the procedure of Synthesis (2) in Example 1 was repeated, giving the desired compound, 2', 4', 6'-trichlorophenyl 10-carboxymethylacridinium-9-carboxylate trifluoromethanesulfonate (hereunder abbreviated as "MAC-18") in an amount of 14 mg.
MS: M+460.

EXAMPLE 18

(1) Synthesis of 2', 3', 6'-trichlorophenyl acridine-9-carboxylate.

The procedure of Synthesis (1) in Example 1 was repeated, except that the starting materials were 9-chlorocarbonylacridine hydrochloride (0.5 g, 1.8 mmol) and 2,3,6-trichlorophenol (0.38 g, 1.9 mmol). As a result, 2', 3', 6'-trichlorophenyl acridine-9-carboxylate was given in an amount of 0.56 g.
$^1$H-NMR: δ7.5–8.7 MS: M+401.

(2) Synthesis of 2', 3', 6'-trichlorophenyl 10-carboxymethylacridinium-9-carboxylate trifluoromethanesulfonate.

Using the 2', 3', 6'-trichlorophenyl acridine-9-carboxylate (20 mg, 0.05 mmol) which was prepared in (1) above, the procedure of Synthesis (2) in Example 1 was repeated, giving the desired compound, 2', 3', 6'-trichlorophenyl 10-carboxymethylacridinium-9-carboxylate trifluoromethanesulfonate (hereunder abbreviated as "MAC-19") in an amount of 41 mg.
MS: M+460.

EXAMPLE 19

(1) Synthesis of 2', 6'-dichloro-4'-fluorophenyl acridine-9-carboxylate.

The procedure of Synthesis (1) in Example 1 was repeated, except that the starting materials were 9-chlorocarbonylacridine hydrochloride ( 0.5 g, 1.8 mmol ) and 2,6-dichloro-4-fluorophenol (0.35 g, 1.9 mmol). As a result, 2', 6'-dichloro-4'-fluorophenyl acridine-9-carboxylate was given in an amount of 0.59 g.
$^1$H-NMR: δ7.3–8.6(10H, m) MS: M+385.

(2) Synthesis of 2', 6'-dichloro-4'-fluorophenyl 10-carboxymethylacridinium-9-carboxylate trifluoromethanesulfonate.

Using the 2', 6'-dichloro-4'-fluorophenyl acridine-9-carboxylate (36 mg, 0.09 mmol) which was prepared in (1) above, the procedure of Synthesis (2) in Example 1 was repeated, giving the desired compound, 2', 6'-dichloro-4'-fluorophenyl 10-carboxymethylacridinium-9-carboxylate trifluoromethanesulfonate (hereunder abbreviated as "MAC-20") in an amount of 50 mg.
MS: M+444.

EXAMPLE 20

( 1) Synthesis of 2', 6'-dibromo-4'-cyanophenyl acridine-9-carboxylate.

The procedure of Synthesis (1) in Example 1 was repeated, except that the starting materials were 9-chlorocarbonylacridine hydrochloride (0.5 g, 1.8 mmol) and 2, 6-dibromo-4'-cyanophenol (0.54 g, 1.9 mmol) . As a result, 2', 6'-dibromo-4'-cyanophenyl acridine-9-carboxylate was given in an amount of 0.64 g.
$^1$H-NMR: δ7.8–8.6( 10H, m) MS: M+482.

(2) Synthesis of 2', 6'-dibromo-4'-cyanophenyl 10-carboxymethylacridinium-9-carboxylate trifluoromethanesulfonate.

Using the 2', 6'-dibromo-4'-cyanophenyl acridine-9-carboxylate (41 mg, 0.08 mmol) which was prepared in (1) above, the procedure of Synthesis (2) in Example 1 was repeated, giving the desired compound, 2', 6'-dibromo-4'-cyanophenyl 10-carboxymethylacridinium- 9-carboxylate trifluoromethanesulfonate (hereunder abbreviated as "MAC-21") in an amount of 24 mg.
MS: M+541.

EXAMPLE 21

(1) Synthesis of 1'-(2'-chloro) naphthyl acridine-9-carboxylate.

The procedure of Synthesis (1) in Example 1 was repeated, except that the starting materials were 9-chlorocarbonylacridine hydrochloride (0.5 g, 1.8 mmol) and 2-chloro-1-naphthol (0.35 g, 1.9 mmol) which was prepared by the method described in Synthesis, p. 582 (1974). As a result, 1'-(2'-chloro) naphthyl acridine-9-carboxylate was given in an amount of 0.55 g.

$^1$H-NMR: $\delta$7.5–8.7( 14H, m) MS: M+383.

(2) Synthesis of 1'-(2'-chloro) naphthyl 10-carboxymethylacridinium-9-carboxylate trifluoromethanesulfonate.

Using the 1'-(2'-chloro) naphthyl acridine-9-carboxylate (37 mg, 0.10 mmol) which was prepared in (1) above, the procedure of Synthesis (2) in Example 1 was repeated, giving the desired compound, 1'-(2'-chloro)-naphthyl 10-carboxymethylacridinium-9-carboxylate trifluoromethanesulfonate (hereunder abbreviated as "MAC-22") in an amount of 53 mg.
MS: M+442.

Comparative Example 1

(1) Synthesis of 3'-methylphenyl acridine-9-carboxylate.

The procedure of Synthesis (1) in Example 1 was repeated, except that the starting materials were 9-chlorocarbonylacridine hydrochloride (0.5 g, 1.8 mmol) and 3-methylphenol (0.21 g, 1.9 mmol). As a result, 3'-methylphenyl acridine-9-carboxylate was given in an amount of 0.48 g.

$^1$H-NMR: $\delta$2.47(3H, s), 7.2–8.4(12H, m) MS: M+313.

(2) Synthesis of 3'-methylphenyl 10-carboxymethylacridinium-9-carboxylate trifluoromethanesulfonate Using the 3'-methylphenyl acridine-9-carboxylate (27 mg, 0.09 mmol) which was prepared in (1) above, the procedure of Synthesis (2) in Example 1 was repeated, giving the desired compound, 3'-methylphenyl 10-carboxymethylacridinium-9-carboxylate trifluoromethanesulfonate (hereunder abbreviated as "MAC-23") in an amount of 42 mg.
MS: M+372.

Comparative Example 2

(1) Synthesis of 4'-methylphenyl acridine-9-carboxylate.

The procedure of Synthesis (1) in Example 1 was repeated, except that the starting materials were 9-chlorocarbonylacridine hydrochloride (0.5 g, 1.8 mmol) and 4-methylphenol (0.21 g, 1.9 mmol). As a result, 4'-methylphenyl acridine-9-carboxylate was given in an amount of 0.47 g.

$^1$H-NMR: $\delta$2.43(3H, s), 7.3–8.4(12H, m) MS: M+313.

(2) Synthesis of 4'-methylphenyl 10-carboxymethylacridinium-9-carboxylate trifluoromethanesulfonate.

Using the 4'-methylphenyl acridine-9-carboxylate (26 mg, 0.08 mmol) which was prepared in (1) above, the procedure of Synthesis (2) in Example 1 was repeated, giving the desired compound, 4'-methylphenyl 10-carboxymethylacridinium-9-carboxylate trifluoromethanesulfonate (hereunder abbreviated as "MAC-24") in an amount of 37 mg.
MS: M+372.

Comparative Example 3

(1) Synthesis of 2'-acetylphenyl acridine-9-carboxylate.

The procedure of Synthesis (1) in Example 1 was repeated, except that the starting materials were 9-chlorocarbonylacridine hydrochloride (0.5 g, 1.8 mmol) and 2-acetylphenol (0.26 g, 1.9 mmol) . As a result, 2'-acetylphenyl acridine-9-carboxylate was given in an amount of 0.42 g.

$^1$H-NMR: $\delta$2.58(3H, s), 7.5–8.5(12H, m) MS: M+341.

(2) Synthesis of 2'-acetylphenyl 10-carboxymethylacridinium-9-carboxylate trifluoromethanesulfonate.

Using the 2'-acetylphenyl acridine-9-carboxylate (27 mg, 0.08 mmol) which was prepared in (1) above, the procedure of Synthesis (2) in Example 1 was repeated, giving the desired compound, 2'-acetylphenyl 10-carboxymethylacridinium-9-carboxylate trifluoromethanesulfonate (hereunder abbreviated as "MAC-25") in an amount of 34 mg.
MS: M+400.

EXAMPLE 22

MAC-2 to MAC-25 which were the acridinium compounds as prepared in Examples 1–24 and phenyl 10-carboxymethylacridinium-9-carboxylate bromide (hereunder abbreviated as "MAC-1") were dissolved in dimethylformamide (DMF) to prepare solutions each having a concentration of $1 \times 10^{-3}$M. These solutions were diluted with PBS (phosphate-buffered saline, pH 6.4) to a concentration of $1 \times 10^{-9}$M. To 10 $\mu$l of each diluted solution, 0.5% hydrogen peroxide in 0.1 N nitric acid (300 $\mu$l ) and 0.125% cetyltrimethylammonium chloride in 0.25 N sodium hydroxide (300 $\mu$l ) were added in that order. The resulting chemiluminescence was measured for 2 seconds with a chemiluminescence analyzer model (AutoCliniLumat LB952 T/16 (Berthold, FRG)) (measurement times longer than 2 seconds are specifically noted in parentheses in Table 1 below), and the quantities of luminescence from the respective compounds are listed in Table 1 in terms of counts per mole.

EXAMPLE 23

MAC-1 to MAC-25 were dissolved in DMF to prepare DMF solutions each having a concentration of $1 \times 10^{-3}$M, which were diluted with PBS to a concentration of $1 \times 10^{-7}$M. The diluted solutions were kept away from light while they were stored at 45° C. for 1 wk. The stored solutions were diluted with PBS to a concentration of $1 \times 10^{-9}$M. The diluted solutions were measured for chemiluminescence as in Example 22 and the percentage of residual emission activity after 1-wk standing was calculated for each test compound according to the following formula (a):

Percentage of residual emission activity =

(Quantity of light emission after 1-wk standing)/

(Quantity of light emission in as-prepared state) $\times$ 100 (%)

The percentage of residual emission activity is a measure for stability and the data for the respective test compounds are shown in Table 1 below.

TABLE 1

| Compound No. | A.X | R¹ | R² | R³ | R⁴ | R⁵ | Light emission ($10^{19}$ counts/M) | Residual emission activity (%) |
|---|---|---|---|---|---|---|---|---|
| MAC-1 | CH₂COOH | H | H | H | H | H | 2.3 | 2 |
| MAC-2 | CH₂COOH | CH₃ | H | H | H | H | 4.6 (5 sec) | 69 |
| MAC-3 | CH₂COOH |  | H | H | H | H | 2.9 | 80 |
| MAC-4 | CH₂COOH | CH₃ | H | H | H | Cl | 2.8 | 32 |
| MAC-5 | CH₂COOH | Cl | H | H | H | Cl | 3.2 | 58 |
| MAC-6 | CH₂COOH | CH₃ | H | NO₂ | H | CH₃ | 1.0 | 80 |
| MAC-7 | CH₂COOH | CH₃ | H | COCH₃ | H | CH₃ | 2.7 | 88 |
| MAC-8 | CH₂COOH | CH₃ | COCH₃ | H | H | CH₃ | 3.1 | 83 |
| MAC-9 | CH₂COOH | CH₃ | H | Cl | H | CH₃ | 2.3 (10 sec) | 90 |
| MAC-10 | CH₂COOH | CH₃ | H | Br | H | CH₃ | 1.1 (10 sec) | 90 |
| MAC-11 | CH₂COOH | CH₃ | H | COCH₃ | —(CH=CH)₂— | | 2.4 | 69 |
| MAC-12 | (CH₂)₄COOH | CH₃ | H | H | H | H | 0.5 | 44 |
| MAC-13 | CH₂COOH | CH₃ | H | F | H | H | 4.3 | 47 |
| MAC-14 | CH₂COOH | CH₃ | H | H | H | NO₂ | 3.2 | 42 |
| MAC-15 | CH₂COOH | Br | H | H | H | Br | 1.6 | 42 |
| MAC-16 | CH₂COOH | F | H | H | H | OCH₃ | 4.4 | 32 |
| MAC-17 | CH₂COOH | CH₃ | H | Cl | H | Cl | 0.5 | 79 |
| MAC-18 | CH₂COOH | Cl | H | Cl | H | Cl | 1.2 | 47 |
| MAC-19 | CH₂COOH | Cl | Cl | H | H | Cl | 1.5 | 83 |
| MAC-20 | CH₂COOH | Cl | H | F | H | Cl | 2.3 | 87 |
| MAC-21 | CH₂COOH | Br | H | CN | H | Br | 1.4 | 31 |
| MAC-22 | CH₂COOH | Cl | H | H | —(CH=CH)₂— | | 1.9 | 66 |
| MAC-23 | CH₂COOH | H | CH₃ | H | H | H | 3.3 | 12 |
| MAC-24 | CH₂COOH | H | H | CH₃ | H | H | 3.2 | 18 |
| MAC-25 | CH₂COOH | COCH₃ | H | H | H | H | 1.9 | 0.3 |

EXAMPLE 24

(1) Preparation of acridinium ester labelled antibody.

MAC-2 which was prepared in Example 1 was dissolved in DMF to a concentration of $1.5 \times 10^{-2}$M. To 80 μl of the solution, a solution (20 μl) of 0.16M N-hydroxysuccinimide in DMF and a solution (20 μl) of 0.12M 1-ethyl-3-(3-dimethylaminopropyl) carbodiimide hydrochloride in a DMF/water (4/6) mixture were added and reaction was carried at room temperature for 3 h. Then, the reaction mixture (7 μl) was added to an anti-hCG monoclonal antibody solution (70 μl) that had been conditioned to 3 mg/ml with a 0.1M sodium carbonate buffer solution (pH 9.5). Following 30-min stirring at room temperature, the reaction mixture was loaded on a Sephadex G-25 column (Pharmacia) and eluted with-PBS to prepare an acridinium-labelled monoclonal antibody.

This monoclonal antibody was loaded on an anion-exchange column using diethylaminoethyl (DEAE) Sepharose (Whatmann) as a carrier and purified by elution on the salt gradient of a 0.005M phosphate buffer solution (pH 8.0). Thereafter, the quantity of luminescence from the purified monoclonal antibody was measured; at the same time, the concentration of protein was measured.

The monoclonal antibody was found to have about one MAC-2 labelled per molecule as a result of calculation from the ratio between the concentration of acridinium ester as determined from the quantity of light emission and the concentration of protein in the antibody.

(2) Preparation of acridinium ester labelled DNA probe.

MAC-2 which was prepared in Example 1 was dissolved in DMF to a concentration of $6 \times 10^{-2}$M. To 40 μl of the solution, a solution (10 μl) of 0.24M N-hydroxysuccinimide in DMF and a solution (10 μl) of 0.18M 1-ethyl-3-(3-dimethylaminopropyl)carbodiimide hydrochloride in a DMF/water (4:6) mixture were added and reaction was performed at room temperature for 3 h. The reaction mixture (8 μl) was added to a solution (20 μl) of an oligomer probe [Hepatitis B virus core region 1941-1970, as synthesized with a 30 mer (HB1010-NH₂(3'))/nucleic acid sequencer] that had been conditioned to 0.15 mg/ml with a 0.1M sodium carbonate buffer solution (pH 9.0). Following 30-min stirring at room temperature, the reaction solution was loaded onto a Sephadex G-25 column (Pharmacia) and eluted with an 8:2 mixture of 0.02M acetate buffer solution (pH 5.5) and acetonitrile, thereby giving labelled HB1010.

The labelled HB1010 was subjected to reverse-phase HPLC and eluted by the gradient of triethylamine acetate/water-acetonitrile. The respective fractions were measured for absorbance at 260 nm and chemiluminescent intensity, and the fractions in which both absorbance and chemiluminescence were high were collected. The collected fractions were desalted by precipitation with ethanol and dissolved in 50 μl of an assay buffer solution [4×SSC (1×SSC=0.15M NaCl, 0.015M sodium citrate), 1×Denhardt's solution (0.02% polyvinyl pyrrolidone, 0.02% Ficoll, 0.02% BSA), 0.2 mg/ml denatured salmon sperm DNA, 0.2% SDS] to prepare an acridinium ester labelled DNA probe.

(3) Chemiluminescent immunoassay with the acridinium ester labelled antibody.

An anti-hCGβ subunit monoclonal antibody (Mochida Pharmaceutical Co., Ltd.) was immobilized on to a polystyrene tube. The tube was charged with 150 μl of an assay buffer solution [10% normal rabbit serum (Pelfreeze), 1% mouse serum (Experimental Animals Association), 0.1% bovine serum albumin (Seikagaku Kogyo Co., Ltd.)/PBS] and 50 μl of hCG standard (1st IRP 75/537) in varying concentrations, and the mixtures were shaken at room temperature for 1 h. Subsequently, washing was done with a washing solution (physiological saline containing 0.005% Tween) three times. The acridinium ester labelled anti-hCG monoclonal antibody which was prepared in (1) above was diluted with an assay buffer solution. Two hundred microliters of the dilution was added to the washed tubes, which were then shaken at room temperature for 1 h. Following three washings with a washing solution, a solution (300 μl) of 0.5% hydrogen peroxide in 0.1N nitric acid was added, followed by the addition of a solution (300 μl) of 0.125% cetyltrimethylammonium chloride in 0.25N sodium hydroxide. The resulting chemiluminescence was measured with a chemiluminescence analyzer model AutoCliniLumat LB952 T/16 (Berthold, FRG) for 2 seconds. By plotting the measured values, a standard curve was constructed as shown in FIG. 1. The detection limit of hCG as determined from this curve was 0.1 IU/L.

(4) Measurement of HBV-DNA using the acridinium ester labelled DNA probe.

Figure 2:
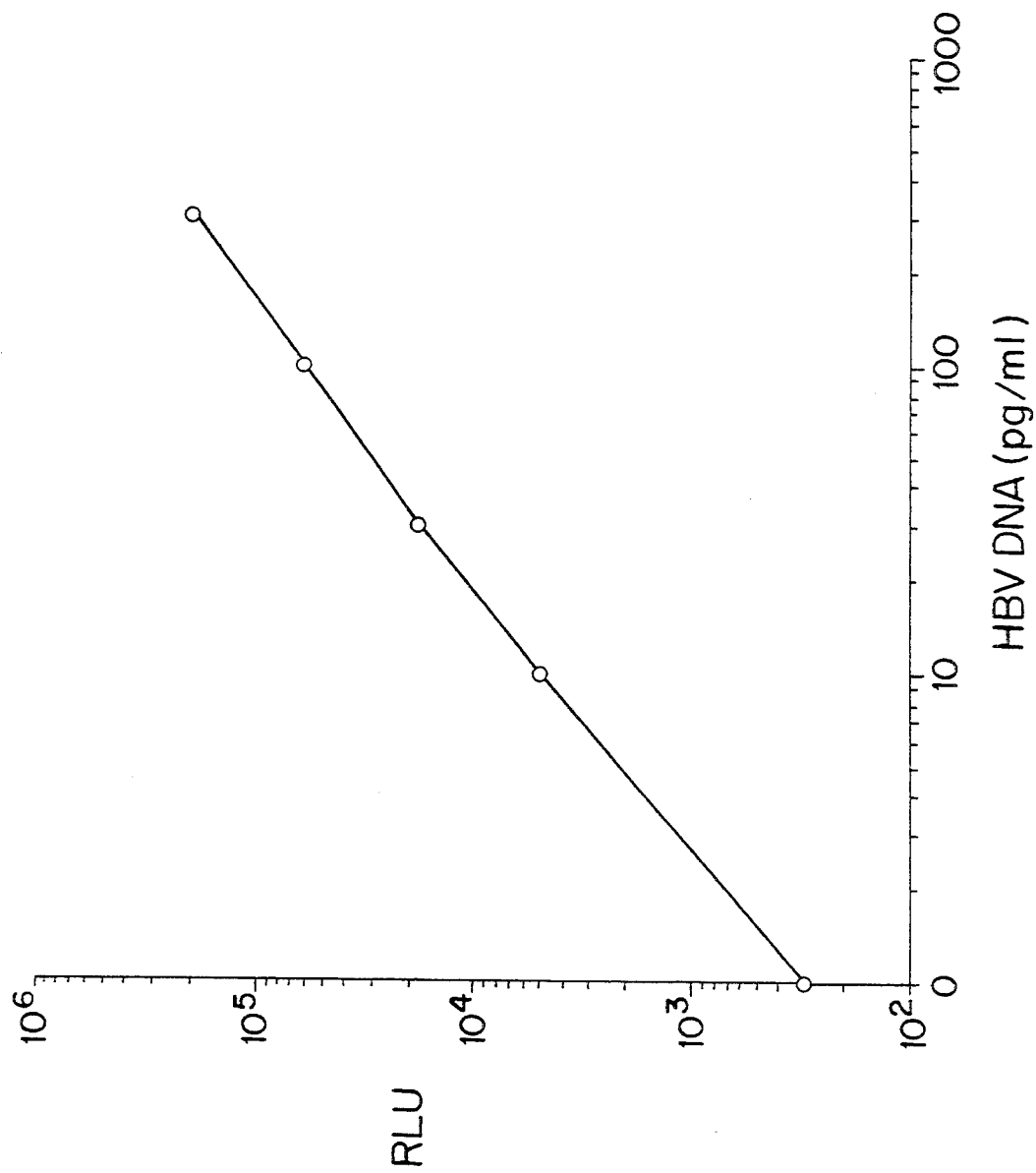
FIG. 2 is a graph showing the result of HBV-DNA measurement using the acridinium ester labelled DNA probe that was prepared in Example 28.

The sequence of HBV-DNA (3.2 kb) was cloned in a pBRHBadr4 vector, from which the 3.2 kb sequence was obtained using a restriction enzyme BamHI and isolated for purification by agarose electrophoresis. The concentration of the thusly obtained HBV-DNA was determined from the absorbance at 260 nm. The HBV-DNA was diluted with a 0.1M Tris-HCl buffer solution (pH 8.0) to prepare standard solutions at concentrations of 1–100 pg/ml. These standard solutions were heat denatured by treatment at 100° C. for 10 rain and, thereafter, they were immobilized by adsorption in a 96-well microtiter plate. After washing, an assay buffer solution (200 μl) was added and preincubated at 60° C. for 1 h. Subsequently, the acridinium ester labelled DNA probe solution which was prepared in (2) above was added to the wells in an amount of $1 \times 10^6$ RLU per well and reaction (hybridization) was performed at 60° C. for 1 h. The supernatant was removed from the reaction mixture and, thereafter, $0.2 \times SSC$ (50° C.) and 0.2% SDS were added, followed by incubation for 5 min (washing). This procedure was repeated five times. The microplate was set up in a chemiluminescence analyzer model Luminous CT-9000D (Chuo Kagaku Kogyo) and a solution (120 μl) of 0.5% hydrogen peroxide in 0.1N nitric acid and then a solution (120 μl) of 0.125% cetyltrimethylammonium chloride in 0.25 N sodium hydroxide were added and the resulting chemiluminescence was measured for 2 seconds. The detection limit was calculated to be 1 pg/ml as shown in FIG. 2.

(5) Stability of the acridinium ester labelled antibody.

The acridinium ester labelled antibody as prepared in (1) above was diluted with an assay buffer solution (PBS containing 10% normal rabbit serum, 1% mouse serum and 0.1% bovine serum albumin) to give an antibody concentration of 0.1 μl/ml. The diluted solution was lyophilizated and then stored at a temperature of 45° C. and a humidity of 90% for 14 days. The stored sample was taken at given time intervals and dissolved in water; the quantity of light emission from the solution was measured as in (3) above but no loss was found to occur in the chemiluminescent activity of the labelled antibody.

(6) Stability of the acridinium ester labelled DNA probe.

The acridinium ester labelled DNA probe as prepared in (2) above was diluted with an assay buffer solution to make a solution having a concentration of 50 ng/ml. A probe was prepared using this solution and its stability under the hybridizing condition (1-h treatment at 60° C.) was checked; about 60% of the initial emission activity was found to have been retained.

The acridinium compounds of the present invention have high emission efficiency and stability; hence, they are useful as a chemiluminescent labelling agent.

The conjugates of the present invention have these acridinium compounds bound to specific binding substances and, hence, they also have high emission efficiency and stability.

What is claimed is:

1. An acridinium compound represented by the general formula (I):

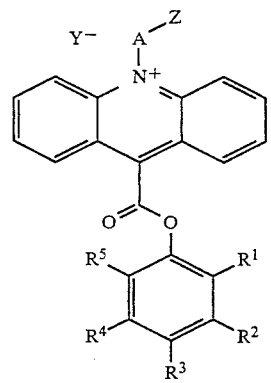

wherein A is an alkylene group having 1–4 carbon atoms or an arylene group, in which one or more carbon atoms may be replaced by hetero atoms or which may optionally have substituents; Z is a carboxyl group, an alkoxycarbonyl group, a carbamoyl group, an aryloxycarbonyl group, a hydroxyl group, a cyano group, a carboxyimide group, an isocyanate group, an isothiocyanate group, an azide group, a sulfonic acid group, a sulfonamide group, a halogenated sulfonyl group, a halogenated carbonyl group, an N-succinimidyloxycarbonyl group or an N-phthalimidyloxycarbonyl group; $R^1$ is a halogen atom, an alkyl group or an aryl group; $R^2$, $R^3$, $R^4$ and $R^5$ which may be the same or different represent a hydrogen atom, an alkyl group, an aryl group, an alkoxy group, an acetyl group, a nitro group, a halogen atom or a carbonyl group, provided that adjacent groups as selected from among $R^2$, $R^3$, $R^4$ and $R^5$ may combine to form a ring; and Y is a counter ion.

2. An acridinium compound according to claim 1 wherein $R^1$ in the general formula (I) is an alkyl group, an aryl group or a halogen, and $R^2$–$R^5$ are each hydrogen.

3. An acridinium compound according to claim 1 wherein $R^1$ in the general formula (I) is an alkyl group, an aryl group or a halogen, $R^5$ is an alkyl group or a halogen, and $R^2$–$R^4$ are each hydrogen.

4. An acridinium compound according to claim 1 wherein $R^1$ in the general formula (I) is an alkyl group, an aryl group or a halogen, either $R^2$ or $R^3$ is a nitro group, an acetyl group or a halogen, $R^5$ is an alkyl group or $R^5$ forms a benzene ring with $R^4$ adjacent to said alkyl group, and the other R's are hydrogen.

5. An acridinium compound according to claim 1 wherein $R^1$ in the general formula (I) is a methyl group and $R^2$–$R^5$ are each hydrogen.

6. An acridinium compound according to claim 1 wherein $R^1$ in the general formula (I) is a phenyl group and $R^2$–$R^5$ are each hydrogen.

7. An acridinium compound according to claim 1 wherein $R^1$ in the general formula (I) is a methyl group, $R^5$ is chlorine, and $R^2$–$R^4$ are each hydrogen.

8. An acridinium compound according to claim 1 wherein $R^1$ and $R^5$ in the general formula (I) are each chlorine and $R^2$–$R^4$ are each hydrogen.

9. An acridinium compound according to claim 4 wherein $R^1$ and $R^5$ in the general formula (I) are each a methyl group, $R^3$ is a nitro group, and $R^2$ and $R^4$ are each hydrogen.

10. An acridinium compound according to claim 1 wherein $R^1$ and $R^5$ in the general formula (I) are each a methyl group, $R^3$ is an acetyl group, and $R^2$ and $R^4$ are each hydrogen.

11. An acridinium compound according to claim 1 wherein $R^1$ and $R^5$ in the general formula (I) are each a methyl group, $R^2$ is an acetyl group, and $R^3$ and $R^4$ are each hydrogen.

12. An acridinium compound according to claim 1 wherein $R^1$ in the general formula (I) is a methyl group, $R^3$ is an acetyl group, and adjacent $R^4$ and $R^5$ fuse to form a benzene ring.

* * * * *